US00PP25764P3

(12) United States Plant Patent
Slaughter et al.

(10) Patent No.: US PP25,764 P3
(45) Date of Patent: Aug. 4, 2015

(54) PEACH TREE NAMED 'BURPEACHTHIRTYFOUR'

(50) Latin Name: *Prunus persica*
Varietal Denomination: Burpeachthirtyfour

(71) Applicants: John K. Slaughter, Fresno, CA (US); Timothy J. Gerdts, Kingsburg, CA (US)

(72) Inventors: John K. Slaughter, Fresno, CA (US); Timothy J. Gerdts, Kingsburg, CA (US)

(73) Assignee: THE BURCHELL NURSERY, INC., Oakdale, CA (US)

( * ) Notice: Subject to any disclaimer, the term of this patent is extended or adjusted under 35 U.S.C. 154(b) by 55 days.

(21) Appl. No.: 13/998,954

(22) Filed: Dec. 27, 2013

(65) Prior Publication Data

US 2015/0189804 P1 Jul. 2, 2015

(51) Int. Cl.
*A01H 5/08* (2006.01)

(52) U.S. Cl.
USPC ..... Plt./198

(58) Field of Classification Search
USPC ..... Plt./198
CPC ..... A01H 5/0868; A01H 5/0837
See application file for complete search history.

*Primary Examiner* — Kent L Bell
(74) *Attorney, Agent, or Firm* — Paine Hamblen, LLP

(57) ABSTRACT

A new and distinct variety of peach tree (*Prunus persica*), and which is denominated varietally as 'Burpeachthirtyfour', and which further produces an attractively colored yellow fleshed, freestone peach which is mature for harvesting and shipment approximately August 16 to August 23 under the ecological conditions prevailing in the San Joaquin Valley of central California.

1 Drawing Sheet

Botanical designation: The present invention relates to a new, novel, and distinct variety of peach tree, *Prunus persica*.
Varietal denomination: 'Burpeachthirtyfour'.

BACKGROUND OF THE NEW VARIETY

The present variety of peach tree resulted from an on-going program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross pollinations each year in order to produce seedling populations from which improved progenies are evaluated and selected.

The seedling, 'Burpeachthirtyfour' was originated by us, and selected from a population of seedlings growing in our experimental orchards which are located near Fowler, Calif. The seedlings, grown on their own roots, were derived from an open pollinated seedling of the 'N9.120' peach tree (unpatented), and which was the seed parent. After a period of stratification, the seed derived from the seed parent was placed in the greenhouse by population, and then field planted for tree establishment, and ultimately to exhibit fruit for evaluation. One yellow fleshed peach seedling, which is the present variety, exhibited especially desirable characteristics, and was then designated as 'Q59.112'. This seedling was marked for subsequent observation. After the 2006 fruiting season, the new variety of peach tree was selected for advanced evaluation and repropagation.

ASEXUAL REPRODUCTION

Asexual reproduction of this new and distinct variety of peach tree was accomplished by budding the new peach tree onto 'Nemaguard' Rootstock (un-patented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachthirtyfour' is a new and distinct variety of peach tree, which is considered of medium-large size, and which has a moderately vigorous growth characteristic. This new tree is also a regular and productive bearer of relatively large, firm, yellow-fleshed, freestone fruit which have a very good flavor, and eating qualities. This new peach tree has a medium chilling requirement of approximately 650 hours, and further produces relatively uniformly sized fruit throughout the tree's canopy. In addition to the foregoing, the fruit produced by the new peach tree also appears to have good handling and shipping qualities. The 'Burpeachthirtyfour' peach tree bears fruit which are typically ripe for commercial harvesting and shipment on approximately August 16 to August 23 under the ecological conditions prevailing in the San Joaquin Valley of central California. In relative comparison to the 'Ryan Sun' peach tree (U.S. Plant Pat. No. 7,829), and which is the closest known variety, the new variety of peach tree bears fruit that exhibits a more rounded shape especially at the apex. Further, and when compared to the 'Ryan Sun' peach tree (U.S. Plant Pat. No. 7,829), the current variety exhibits a minimal amount of preharvest fruit drop. In relative comparison to the seed parent, 'N9.120' peach tree, the present variety ripens approximately 2 weeks earlier.

BRIEF DESCRIPTION OF THE DRAWINGS

The accompanying drawing, which is provided, is a color photograph of portions of the new peach tree variety. The photograph depicts two whole mature fruit viewed from the apical aspect. One mature fruit is shown, and which is bisected transversely through the equatorial plane, and which reveals the flesh color, and stone characteristics thereof. The external coloration of the fruit as shown in the photograph is sufficiently matured for harvesting and shipment. Additionally, the photograph displays a sample vegetative shoot bearing typical leaves, and a typical stone with the flesh removed. The colors in this photograph are as nearly true as is reasonably possible in a color representation of this type. Due to chemical development, processing and printing, the leaves and fruit depicted in this photograph may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the seventh fruiting season, and under the ecological conditions prevailing at the orchards of the assignee which are located near the town of Fowler, county of Fresno, state of California. All major color code designations are by reference to The R.H.S. Colour Chart (Fourth Edition, 2001) provided by The Royal Horticultural Society of Great Britain. Common color names are also occasionally used.

TREE

*Size.*—Generally considered medium to medium-large in its growth pattern as compared to other common commercial peach cultivars ripening in the late season of maturity. The tree of the present variety was pruned to a height of approximately 270.0 cm. to about 310.0 cm. at commercial maturity.

*Width.*—Approximately 275.0 cm.

*Vigor.*—Considered moderately vigorous. The present peach tree variety grew from about 170.0 cm. to about 180.0 cm. in height during the first growing season. The new variety was pruned to a height of approximately 150.0 cm. during the first dormant season, and primary scaffolds were then selected for the desired tree structure.

*Productivity.*—Productive. Fruit set varies from more than the desired crop load, to levels higher than desired levels, when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

*Fruit bearing.*—Regular. Fruit set has been more than adequate during the previous years of observation, and thinning was necessary during the past 7 years on both the original seedling, and on subsequent asexually reproduced trees.

*Tree form.*—Upright, and pruned into a vase shape.

*Density.*—Considered moderately dense. It has been discovered that pruning the branches from the center of the tree to obtain a resulting vase shape allows for enhanced air movement and appropriate amounts of sunlight to reach the tree, and which improves the resulting fruit color, and the renewal of fruiting wood throughout the tree.

*Hardiness.*—The present tree was grown, and evaluated in USDA Hardiness Zone 9. The calculated winter chilling requirements of the new tree is approximately 650 hours at a temperature below 7.0 degrees C. The present variety appears to be hardy under typical central San Joaquin Valley climatic conditions.

TRUNK

*Diameter.*—Approximately 17.5 cm in diameter when measured at a distance of approximately 15.24 cm. above the soil level. This measurement was taken at the end of the 7th growing season.

*Bark texture.*—Considered moderately rough, with numerous folds of papery scarfskin being present. Since bark development, and coloration change with advancing tree age this characteristic varies with the tree vigor, age and regional conditions. Therefore, this is not a reliable descriptor of the new variety.

*Lenticels.*—Numerous flat, oval lenticels are present. The lenticels range in size from approximately 4.0 millimeters to about 6.0 mm. in width, and between about 1.0 mm and about 2.0 millimeters in height. The development, and size of the trunk lenticels, can be influenced, to some degree, by the ambient growing conditions, and are not, necessarily, a dependable and distinguishing characteristic of this variety. As trees of this variety mature, lenticels are present, but they are generally covered by increasing layers of cork (mature bark) and therefore become less apparent.

*Lenticel color.*—Considered an orange brown, (RHS Greyed-Orange Group N167 C).

*Bark coloration.*—Variable, but it is generally considered to be a greyed brown, (RHS Grey Group 201 D). This bark description was taken from trees in their seventh leaf which have ruptured the scarf skin, and which also have developed bark furrowing which is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

*Size.*—Considered medium for the variety.

*Diameter.*—Average as compared to other peach varieties. The branches have a diameter of about 10.0 centimeters when measured during the 6th year after grafting.

*Surface texture.*—Average, and appearing furrowed on wood which is several years old.

*Crotch angles.*—Primary branches are considered variable, and are usually observed by growing at an angle of about 45 to about 57 degrees when measured from a horizontal plane. This characteristic can be influenced, to some degree, by tree vigor, rootstock and other cultural conditions.

*Current season shoots.*—Surface texture — Substantially glabrous.

*Internode length.*—Approximately 2.3 cm.

*Color of mature branches.*—Grey brown, (RHS Grey Group 201 D).

*Current seasons shoots.*—Color. — Medium-light green, (RHS Yellow-Green Group 146 A). The color of new shoot tips is considered a bright and shiny green (RHS Yellow-Green Group 146 D). The vegetative shoot color can be significantly influenced by plant nutrition, irrigation practices, and exposure to sunlight, and therefore should not be considered a consistent nor distinctive botanical characteristic of this new variety.

LEAVES

*Size.*—Considered medium-large for the species. Leaf measurements have been taken from vigorous, upright, current-season growth, at approximately mid-shoot. It should be understood that the resulting leaf size is often influenced by the prevailing growing conditions, quality of sunlight, and the location of the leaf within the tree canopy. For this reason, leaf sizes can vary significantly based upon the ambient, and other cultural factors listed above, and are not typically considered a dependable botanical descriptor.

*Leaf length.*—Approximately 158.0 to about 165.0 millimeters.

*Leaf width.*—Approximately 35.0 to about 42.0 millimeters.

*Leaf base-shape.*—The leaves generally exhibit equal marginal symmetry relative to the leaf longitudinal axis.

*Leaf form.*—Lanceolate.

*Leaf tip form.*—Acuminate.

*Leaf color.*—Upper Leaf Surface — Dark green, (approximately RHS Green Group 137 C).

*Leaf texture.*—Glabrous.

*Leaf color.*—Lower Leaf Surface — light to medium green, (approximately RHS Green Group 137 D).

*Leaf venation.*—Pinnately veined.

*Mid-vein.*—Color — Considered a light, yellow-green, (approximately RHS Yellow-Green Group 144 C) in the early to mid-period of the growing season.

*Leaf margins.*—Gently undulating. Form. — Considered crenate. Uniformity. — Considered generally uniform.

*Leaf petioles.*—Form. — Considered canaliculated, and having a more pronounced trough when viewed from the dorsal aspect. The petiole margin is considered rounded when viewed from the ventral aspect. Size. — Considered medium-small for the species. Length. — About 8.0 to about 11.0 mm. Diameter. — About 1.5 to about 2.0 mm. Color. — Light yellow green, (appoximately RHS Yellow-Green Group 144 C).

*Leaf glands.*—Size. — Generally considered small for the species; approximately 1.0 mm. in length; and about 1.0 mm. in height. Number. — Generally one to two glands per marginal side are found. Observations of more than two glands per marginal side are much more uncommon. Type. — The glands are located at the base of the leaf, and are predominantly reniform in shape. An additional one, two, or occasionally more glands, which appear more globose, and stalked, are often present at the basal margin of the leaf petiole as well. Color. — Considered a medium, light brown, approximately (RHS Grey-Brown Group 199 B). Typically the coloration of the glands darkens, and occasionally begins to desiccate during, and thereafter, the mid-late growing season.

*Leaf stipules.*—Size. — Medium large for this variety. Number. — Typically 2 per leaf bud, and up to 6 per shoot tip. Form. — Lanceolate in form, and having a serrated marginal edge. Color. — Green, (approximately RHS Green Group 139 B) when young, but graduating to a brown color, (approximately RHS Greyed-Orange Group 165 A) with advancing senescence. The leaf stipules are generally considered to be early deciduous.

FLOWER BUDS

*Hardiness.*—No winter injury (bud death) has been noted during the last several years of observation in the central San Joaquin Valley. The new variety of peach tree has not been intentionally subjected to drought, cold or heat stress, and therefore this information is not available.

*Flower bud.*—Size — Variable, and dependent upon the state of maturity. The flower buds as described were observed approximately 7 days prior to bloom.

*Flower bud.*—Length — Approximately 14.0 millimeters.

*Flower bud.*—Diameter — Approximately 9.0 millimeters.

*Flower bud surface texture.*—Pubescent.

*Flower bud orientation.*—Considered appressed, but may appear less so as the blossoms near opening.

*Bud scale color.*—Approximately (RHS Greyed-Purple N186 C).

FLOWERS

*Date of first bloom.*—Observed on Mar. 2, 2013.

*Blooming time.*—Considered average in relative comparison to other commercial peach cultivars grown in the central San Joaquin Valley. The date of full bloom was observed on Mar. 8, 2013. The date of full bloom varies slightly based upon the surrounding climatic conditions, and the prevailing cultural practices.

*Duration of bloom.*—Approximately 7 days and sometimes more. This particular characteristic varies slightly with the prevailing climatic conditions.

*Flower class.*—Considered a perfect flower, complete and perigynous.

*Flower type.*—The variety is considered to have a showy type flower.

*Flower size.*—Considered medium. The flower diameter at full bloom, is approximately 30.0 to 35.0 millimeters.

*Bloom quantity.*—Considered abundant.

*Flower bud frequency.*—Normally two flower buds appear per node. Occasionally one flower bud per node is observed. From time-to-time more than two flower buds per node are observed.

*Petal size.*—Generally considered medium for the species.

*Petal length.*—Approximately 13.0 to 17.0 millimeters.

*Petal width.*—Approximately 12.0 to 15.0 millimeters.

*Petal form.*—Considered broadly ovate.

*Petal count.*—Nearly always 5.

*Petal texture.*—Glabrous.

*Petal color.*—Considered a light pink at the popcorn stage, (RHS Red Group 49 B), and darkening with advanced senescence, and the exposure of sunlight, to a medium-dark pink, (RHS Red-Purple 63 C).

*Fragrance.*—Slight.

*Petal claw.*—Form. — The claw is considered truncate, and is generally considered medium-small when as compared to other varieties. Length. — Approximately 6.0-7.0 millimeters. Width. — Approximately 6.0 to 8.0 millimeters.

*Petal margins.*—Generally considered variable, from nearly smooth to moderately undulate and ruffled, especially apically.

*Petal apex.*—Generally, the petal margin is entire at the tip.

*Flower pedicel.*—Length. — Considered medium-long with an approximate length of about 2.5 to about 3.0 millimeters. Diameter. — Approximately 2.0 millimeters. Color. — A medium brown, approximately (RHS Grey-Brown Group 199 A). Surface. — Glabrous.

*Floral nectaries.*—Color. — Considered a deep orange (approximately RHS Greyed-Orange Group N172 B).

*Calyx.*—Surface Texture. — Generally glabrous. Color. — A dull red, (approximately RHS Greyed-Purple Group 183 A).

*Sepals.*—Surface Texture. — The surface has a short, fine pubescent texture. Number. — 5 sepals Size. — Average, and ovate in form. Sepal Length. — Approximately 4.0 to 6.0 millimeters. Sepal Width. — Approximately 4.0 to 6.0 millimeters. Sepal Shape. — Generally obovate. Sepal Margin. — Considered smooth and entire. Sepal Color. — A dull, magenta, (approximately RHS Greyed-Red Group 181 C).

*Anthers.*—Generally. — Average in size. Color. — Red to reddish-orange when viewed dorsally and prior to dehiscence, (approximately RHS Greyed-Red Group 179 A).

*Pollen production.*—Pollen is abundant and has a yellow color, (approximately RHS Yellow-Orange Group 17 B).

*Fertility.*—Self-fertile.

*Filaments.*—Size. — Approximately 13.0 to 15.0 millimeters in length. Color. — Considered white to a pinkish-white, (RHS Red Purple Group 65 C).

*Pistil.*—Number. — Usually one, and only rarely more than one. Generally. — Large in size. Length. — Approximately 16.0 to about 18.0 millimeters in length including the ovary. Color. — Considered a very pale green, (approximately RHS Yellow-Green Group 150 C). Surface Texture. — The variety has a long pubescent pistil.

FRUIT

*Maturity when described.*—Firm ripe condition (shipping ripe).

*Date of first picking.*—Approximately Aug. 16, 2013. Date of last picking. — Aug. 23, 2013. The date of harvest can vary slightly with the prevailing climatic conditions, and the currently employed cultural practices.

*Size.*—Generally — Considered large, and uniform.

*Average cheek diameter.*—Approximately 73.0 to about 89.0 millimeters.

*Average axial diameter.*—Approximately 70.0 to about 87.0 millimeters.

*Typical weight.*—Approximately 235.0 grams. This weight characteristic is quite dependent upon the prevailing cultural practices, and therefore is not particularly distinctive of the new variety.

*Fruit form.*—Generally — Considered globose. The fruit is generally uniform in symmetry.

*Fruit suture.*—No stitching exists along the suture line.

*Suture.*—Color — Generally, the fruit appears blushed to the same degree as the skin, (approximately Orange-Red Group RHS N34 A).

*Ventral surface.*—Form — Quite even, and uniform in appearance, when it is viewed from the lateral, sutural plane.

*Apex.*—Shape — Rounded to slightly retuse.

*Base.*—Shape — Generally smooth.

*Stem cavity.*—Generally — This feature extends in a rounded circular form which is generally considered uniform. The stem cavity, as noted, above, is rounded but extends slightly toward the suture. The average depth of the stem cavity is about 6.0-9.0 mm. The average width of the stem cavity is about 20.0 mm. The average length of the stem cavity, when measured in the suturial plane. is about 35.0 mm.

*Fruit skin.*—Thickness. — Considered medium in thickness, and tenacious to the flesh. Surface Texture. — Short, fine and pubescent. The pubescence is moderately abundant. Taste. — Non-astringent. Tendency to crack. — Not observed in the previous years of observation and evaluation.

*Fruit skin color.*—Blush Color. — Generally speaking, a red blush exists on a majority of the skin of the fruit (approximately RHS Orange-Red Group N34 A), and is more typically present on the portions of the fruit facing the sunlight. The blush of the fruit typically covers approximately 65%-85% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown. Ground Color. — Yellow, (approximately RHS Yellow Group 13 A). The ground color of the fruit can vary significantly based upon the maturity of the fruit when this measurement is taken.

*Fruit stem.*—Size. — Medium in length, approximately 6.0 to about 8.0 millimeters. Diameter. — Approximately 2.0 to about 3.0 millimeters. Color. — Pale yellow-green, (approximately RHS Yellow-Green Group N144 B).

*Fruit flesh*.—Ripening. — Considered even. Texture. — Firm, juicy and dense. Considered firm yet non-melting. Fibers. — Present but not prominent. Aroma. — Slight. Eating Quality. — Considered very good. Flavor. — Considered very sweet, and with moderate acidity. The flavor is considered both pleasant and balanced. Juice Production. — Moderate. Brix. — About 11.5 to 13.0 degrees. This characteristic varies slightly with the number of fruit per tree; the maturity of fruit when harvested; the prevailing cultural practices; and the ambient climatic conditions. Acidity. — Approximately 0.7-0.8 titratible acidity was detected. Flesh Color. — Considered a deep yellow, (approximately RHS Yellow- Orange Group 21 A).

STONE

*Type*.—Considered a freestone.

*Size*.—The stone size is generally considered to be medium for the variety. The stone size can further vary, significantly, depending upon the tree vigor, the crop load, and the prevailing growing and cultural conditions under which the tree was grown.

*Length*.—Average, about 27.0 to about 30.0 millimeters.

*Width*.—Average, about 22.0 to about 26.0 millimeters.

*Diameter*.—Average, about 17.0 to about 19.0 millimeters.

*Form*.—Roughly ovoid.

*Stone base*.—Shape — The stone is considered shortly attenuate.

*Apex*.—Shape — The stone exhibits a slight apex.

*Stone surface*.—Surface Texture — Considered irregularly furrowed toward the apex and along the stone's edge. Pitting is prominent, in general, over the exterior surface. Ridges. — Ridging is generally more prominent, and is usually oriented parallel, and laterally relative at the ventral and dorsal margins. Ventral Edge. — The ventral edge is generally considered troughed with three substantial grooves that converge apically. Dorsal Edge. — Shape — Generally considered even. The folds of the surface ridges appearing on the external margins often end gently along the suture.

*Stone color*.—The color of a mature, dry stone is generally considered a dull brown, approximately (RHS Greyed-Orange Group 177 A).

*Tendency to split*.—Splitting has only rarely been noted.

*Kernel*.—Length. — Approximately 18.0-21.0 millimeters. Width. — Approximately 12.0-15.0 millimeters. Thickness. — 4.0-5.0 millimeters. Size. — The kernel is considered medium in size. Further the kernel is gelatinous and immature when the fruit is fully mature, and ready for harvesting and shipment. Form. — Considered generally ovoid. Pellicle. — Slightly pubescent. Color. — A dark tan (RHS Greyed-Orange Group 164 A).

*Use*.—The present variety 'Burpeachthirtyfour' is considered to be a peach tree of the late mid-season of maturity, and which further produces fruit which are considered to be firm, attractively colored, and which are useful for both local, and long distance shipping.

*Keeping quality*.—Appears excellent. The fruit of the present variety has stored well for periods of up to 30 days after harvest at 1.0 degree Celsius.

*Shipping quality*.—Good. The fruit of the new peach tree variety showed minimal bruising of the flesh or skin damage after being subjected to normal harvesting and packing procedures.

*Resistance to insects and disease*.—No particular susceptibilities were noted. The present variety has not been intentionally tested to expose or detect any susceptibilities or resistances to any known plant, fruit diseases, insect, frost, winter injury or other environmental factors.

Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new and distinct variety of peach tree, substantially as illustrated and described, and which is characterized principally as to novelty by producing an attractively colored yellow fleshed, freestone peach which is mature for harvesting and shipment approximately August 16 to August 23 under the ecological conditions prevailing in the San Joaquin Valley of central California.

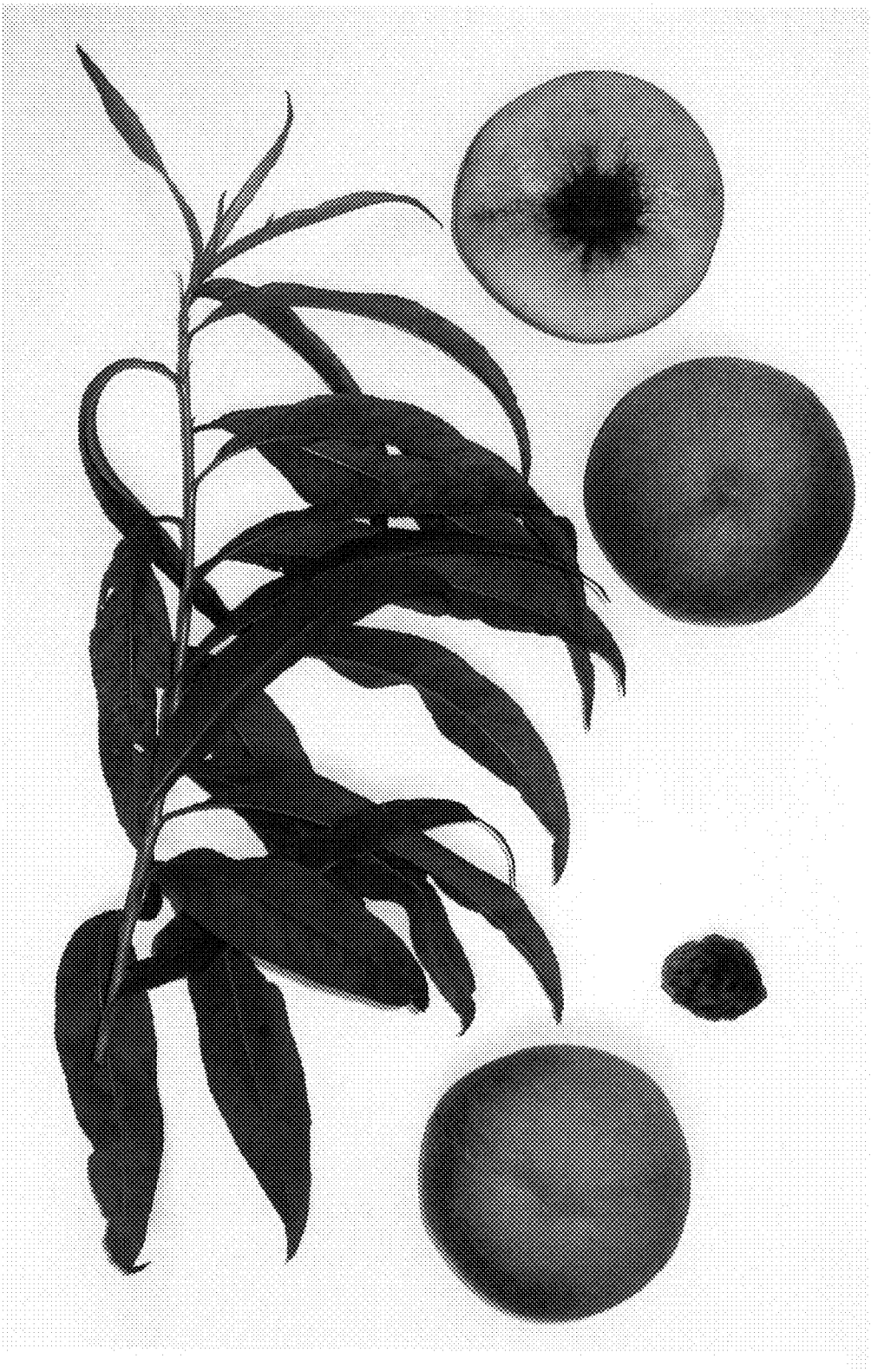

* * * * *